United States Patent
Ferrero, V

(10) Patent No.: US 12,071,451 B2
(45) Date of Patent: Aug. 27, 2024

(54) SYSTEMS INCLUDING SIMULATED MOVING BED SEPARATORS FOR HIGH PURITY FRUCTOSE PRODUCTION AND RELATED METHODS

(71) Applicant: Amalgamated Research LLC, Twin Falls, ID (US)

(72) Inventor: Peter Thomas Ferrero, V, Jerome, ID (US)

(73) Assignee: Amalgamated Research LLC, Twin Falls, ID (US)

( * ) Notice: Subject to any disclaimer, the term of this patent is extended or adjusted under 35 U.S.C. 154(b) by 420 days.

(21) Appl. No.: 17/307,609

(22) Filed: May 4, 2021

(65) Prior Publication Data

US 2021/0347801 A1  Nov. 11, 2021

Related U.S. Application Data

(60) Provisional application No. 63/020,390, filed on May 5, 2020.

(51) Int. Cl.
| | | |
|---|---|---|
| *C13K 1/00* | (2006.01) | |
| *B01D 15/18* | (2006.01) | |
| *C07H 1/08* | (2006.01) | |
| *C07H 3/02* | (2006.01) | |
| *C12P 19/02* | (2006.01) | |
| *C13B 20/16* | (2011.01) | |
| *C13B 25/00* | (2011.01) | |
| *C13K 11/00* | (2006.01) | |

(52) U.S. Cl.
CPC ............. *C07H 1/08* (2013.01); *B01D 15/185* (2013.01); *C07H 3/02* (2013.01); *C12P 19/02* (2013.01); *C13K 11/00* (2013.01)

(58) Field of Classification Search
CPC ..... C13B 25/00; C13B 20/14; B01D 15/1821; C13K 1/00
See application file for complete search history.

(56) References Cited

U.S. PATENT DOCUMENTS

| | | | |
|---|---|---|---|
| 3,513,023 A | 5/1970 | Kusch et al. | |
| 3,928,062 A | 12/1975 | Yamauchi | |
| 4,938,804 A | 7/1990 | Heikkila et al. | |
| 5,102,553 A | 4/1992 | Kearney et al. | |
| 5,122,275 A | 6/1992 | Rasche | |
| 5,656,094 A | 8/1997 | Peckous | |
| 6,299,694 B1 | 10/2001 | Ma | |
| 6,602,420 B2 | 8/2003 | Kearney et al. | |
| 7,931,751 B2 | 4/2011 | Costesso et al. | |
| 8,524,888 B2 | 9/2013 | Lee et al. | |
| 10,569,195 B2 * | 2/2020 | Binder | C13K 1/08 |
| 2013/0317210 A1 | 11/2013 | Oroskar et al. | |
| 2014/0275518 A1 | 9/2014 | Oroskar et al. | |
| 2020/0047083 A1 | 2/2020 | Antharavally et al. | |

FOREIGN PATENT DOCUMENTS

| | | |
|---|---|---|
| CN | 104744523 A | 7/2015 |
| EP | 3560571 A | 10/2019 |
| WO | WO0187452 A | 11/2001 |
| WO | 2016/160573 A1 | 10/2016 |

OTHER PUBLICATIONS

Bucke "Enzymes in Fructose Manufacture" Tate & Lyle, Reading, UK, pp. 51-72 (1981).
Zhang et al: "Modified reactive SMB for production of high concentrated fructose syrup by isomerization of glucose to fructose", Biochemical Engineering Journal, Elsevier, Amsterdam, NL, vol. 35, No. 3, (May 31, 2007), pp. 341-351, XP022100399, ISSN:1369-703X, DOI: 10.1016/J.BEJ.2007.01.026 May 31, 2007.
Mallmann T et al: "Standing wave design of nonlinear SMB systems for fructose purification", Aiche Journal, John Wiley & Sons, Inc, US, vol. 44, No. 12, 1 (Apr. 16, 2004), pp. 2628-2646, XP071000451, ISSN: 0001-1541, DOI: 10.1002/AIC.690441206 Apr. 16, 2004.
European Patent Office; International Search Report and Written Opinion for Application No. PCT/US2021/030636 dated Sep. 20, 2021.

* cited by examiner

*Primary Examiner* — Maryam Monshipouri
(74) *Attorney, Agent, or Firm* — Dorsey & Whitney LLP

(57) ABSTRACT

A method of enriching a material comprising glucose, fructose, and one or more components inert to isomerization using chromatography to produce a high purity fructose product. An embodiment of the method purifies high fructose corn syrup from a feedstock into three product streams: a first fraction rich in glucose, a second fructose product comprising an extract of fructose purity exceeding about 95%, and a third less pure fructose fraction comprising fructose ranging from about 55% to about 90% fructose purity. The third less pure fructose fraction may be combined with 42% fructose syrup to produce saleable mid-purity fructose product, such as having 55% fructose purity. An SMB system is also disclosed and comprises a first SMB separator, a second SMB separator, and an isomerization chamber.

13 Claims, 3 Drawing Sheets

SYSTEMS INCLUDING SIMULATED MOVING BED SEPARATORS FOR HIGH PURITY FRUCTOSE PRODUCTION AND RELATED METHODS

CROSS-REFERENCE TO RELATED APPLICATION

This application claims the benefit under 35 U.S.C. § 119(e) of U.S. Provisional Patent Application Ser. No. 63/020,390, filed May 5, 2020, the disclosure of which is hereby incorporated herein in its entirety by this reference.

TECHNICAL FIELD

Embodiments disclosed herein relate to simulated moving bed (SMB) chromatographic separators for purification of a feedstock. More particularly, embodiments of the disclosure relate to methods of enriching a feedstock containing glucose, fructose, and components inert to isomerization into a fructose extract comprising greater than about 95% fructose purity and to related SMB chromatographic separators and systems.

BACKGROUND

Over the past forty years, blended syrups containing fructose have emerged as a liquid sweetener alternative to sucrose in the food and beverage industry. Common methods to produce fructose include the inversion of sucrose and the isomerization of dextrose syrup, typically derived from corn starch. For either of these methods, incomplete hydrolysis of sucrose or starch will produce a ternary mixture of glucose, fructose, and higher polysaccharides (also denoted here as "DP2+" where "DP" means "degree of polymerization" and "X+" refers to oligosaccharides comprising of "X" or more monosaccharide units) depending on the source material.

Simulated moving bed chromatography has been used to produce a fructose-rich extract of approximately 80% to 90% fructose purity. In the corn sweetener industry, HFCS-42 (HFCS-X denotes a high fructose corn syrup stream containing 'X' percent of fructose on a dry solids basis) obtained via the isomerization of dextrose syrup is used to produce HFCS-90 which is then blended downstream with HFCS-42 to produce HFCS-55 which is used as a liquid sweetener. The main operating cost of this SMB process is the energy used to concentrate the blended HFCS-55 to a final dissolved solids ("DS") content of 78% (w/w). The HFCS-55 market has matured in the forty years since being introduced to consumers. As consumers continue to demand natural sweeteners over those viewed as being highly processed, such as HFCS-55, pressure will be applied to the corn sweetener industry to develop alternative uses for HFCS.

Conventionally, when using an SMB to process HFCS-42, two fractions are produced: a 80% to 90% pure fructose-rich extract and a raffinate stream containing 80%-90% glucose on a dry solids basis. In order to increase the conversion of glucose into fructose, it is economically advantageous to recycle the glucose-rich raffinate to isomerization columns. These columns contain the immobilized enzyme xylose isomerase (colloquially known as glucose isomerase), which is able to convert approximately 50% of the glucose to fructose at equilibrium depending on the process temperature. However, the time required for the isomerization reaction to reach equilibrium causes an unacceptable loss in throughput through the isomerization chamber. Thus, a compromise between conversion and throughput is made to produce HFCS of 42% to 46% fructose purity.

Higher purity fructose is desirable as a low-calorie nutritive sweetener or as raw inputs to produce other high-value materials such as allulose. Conventional methods for producing high purity fructose may involve crystallizing a liquid stream containing about 95% fructose on a dry solids basis. The fructose crystals are produced by adding an excess of ethanol to a highly concentrated fructose syrup at a dry solids content in excess of 90%. In addition to the disadvantages of handling organic solvents for the crystallization process, the concentration of the fructose syrup to 90%-95% DS is energy intensive, especially for applications where the crystalline product is then redissolved for further processing.

Aqueous-based processes for crystallizing fructose are also known. While avoiding the need for using organic solvents, a high input of energy is used to concentrate the fructose syrup to promote the controlled formation of fructose crystals. Additionally, the yield of fructose crystals ranges from 45% to 65%, producing a high purity mother liquor that is typically blended with HFCS-42 to produce HFCS-55 sweetener as a by-product. Recycling the mother liquor is not feasible due to the accumulation of color during multiple crystallization passes which yield non-saleable fructose crystals.

An integrated process to produce HFCS-42, HFCS-55, and crystalline fructose is also known and maximizes the yield of saleable solid and liquid fructose sweetener. However, recent trends in consumer preferences have lowered the demand for low-purity HFCS sweeteners produced as a by-product in this process. Furthermore, for applications where high purity fructose is further converted into higher-value chemicals such as allulose, 5-(hydroxymethyl)-2-furfural (HMF), and furfural, the capital and operating costs associated with crystallization reduce the economic viability of using crystalline fructose as a raw material.

The oligosaccharide content is an additional factor to be considered when the SMB-produced glucose-rich raffinate constitutes a portion of the feed to the isomerization chamber. The SMB raffinate is not pure glucose and contains a fraction of oligosaccharides which are inert during glucose isomerization. Repeated recycling of the glucose-rich raffinate causes the oligosaccharides to accumulate in the isomerization chamber feed, which will preclude glucose isomerase from producing HFCS of 42% purity once the dry solids content of glucose in the isomerization feed falls below roughly 84%. In addition to limiting the equilibrium purity of the HFCS isomerization product, the time required to produce HFCS-42 increases with the level of oligosaccharides in the isomerization feed, which severely reduces the throughput of the isomerization unit. Processing HFCS-42 with increased oligosaccharide content also increases the water requirements of the SMB in order to maintain a fructose extract purity of 90% or greater, which significantly affect the energy costs of evaporating the fructose extract. Thus, it is highly beneficial for overall factory fructose production to limit the oligosaccharide content in the glucose feed to isomerization. Conventionally, a fraction of the SMB raffinate is purged from the process to control the levels of oligosaccharides present in the isomerization feed.

The issue of oligosaccharide accumulation in the isomerization feed due to SMB raffinate recycle is further exacerbated when producing fructose extract of 97% purity or higher. In conventional processing, the 90% purity fructose extract contains about 4% oligosaccharides with the remainder being glucose. As a result, the fructose extract serves as a second outlet to reduce the oligosaccharide content of the isomerization feed. However, as the purity requirements of the fructose extract increase, the effectiveness of this second bleed stream decreases as more of the oligosaccharides are partitioned into the raffinate stream in order to increase the extract purity. Due to this, the oligosaccharide content of the feed into isomerization will greatly increase which will significantly lower the fructose productivity of isomerization. The only option for a conventional process is to lower the amount of SMB raffinate recycled to isomerization, which results in less glucose being converted to fructose and decreases the overall profitability of the plant.

BRIEF SUMMARY

The disclosure comprises a method for producing a high-purity fructose product. The method comprises introducing a feed stream comprising glucose and fructose to an isomerization chamber to produce an isomerized product. The isomerized product is introduced to a first simulated moving bed (SMB) separator to produce a fructose fraction and a glucose fraction. The glucose fraction is introduced to the isomerization chamber to produce additional isomerized product. The fructose fraction is introduced to a second SMB separator to produce a high purity fructose product exhibiting a purity of greater than or equal to about 90% by weight. The high purity fructose product is recovered.

The disclosure comprises a method of producing a high purity fructose stream. The method comprises introducing a feedstock comprising glucose, fructose, and one or more components inert to isomerization to fructose to a first simulated moving bed (SMB) separator of an SMB system to produce a fructose extract and a glucose-rich raffinate. The glucose-rich raffinate is introduced to an isomerization chamber to produce additional fructose. The fructose extract is introduced to a second SMB separator to produce a high purity fructose extract exhibiting a purity of greater than or equal to about 95% by weight and a fructose raffinate. The high purity fructose extract is recovered.

The disclosure also comprises a system that comprises a first SMB separator, a second SMB separator, and an isomerization chamber, wherein the first SMB separator and the second SMB separator are coupled in series. The first SMB separator is configured to produce a fructose extract and a glucose-rich raffinate from a feed stream. The isomerization chamber is configured to receive the glucose-rich raffinate and the feed stream and to produce an isomerized product comprising fructose. The second SMB separator is configured to receive the fructose extract and to produce a high purity fructose extract that exhibits a fructose purity of greater than or equal to about 95% by weight.

BRIEF DESCRIPTION OF THE DRAWINGS

While the specification concludes with claims particularly pointing out and distinctly claiming that which is regarded as the present invention, the advantages of this invention may be more readily ascertained from the following description of the invention when read in conjunction with the accompanying drawings in which:

DETAILED DESCRIPTION

Figure 1:
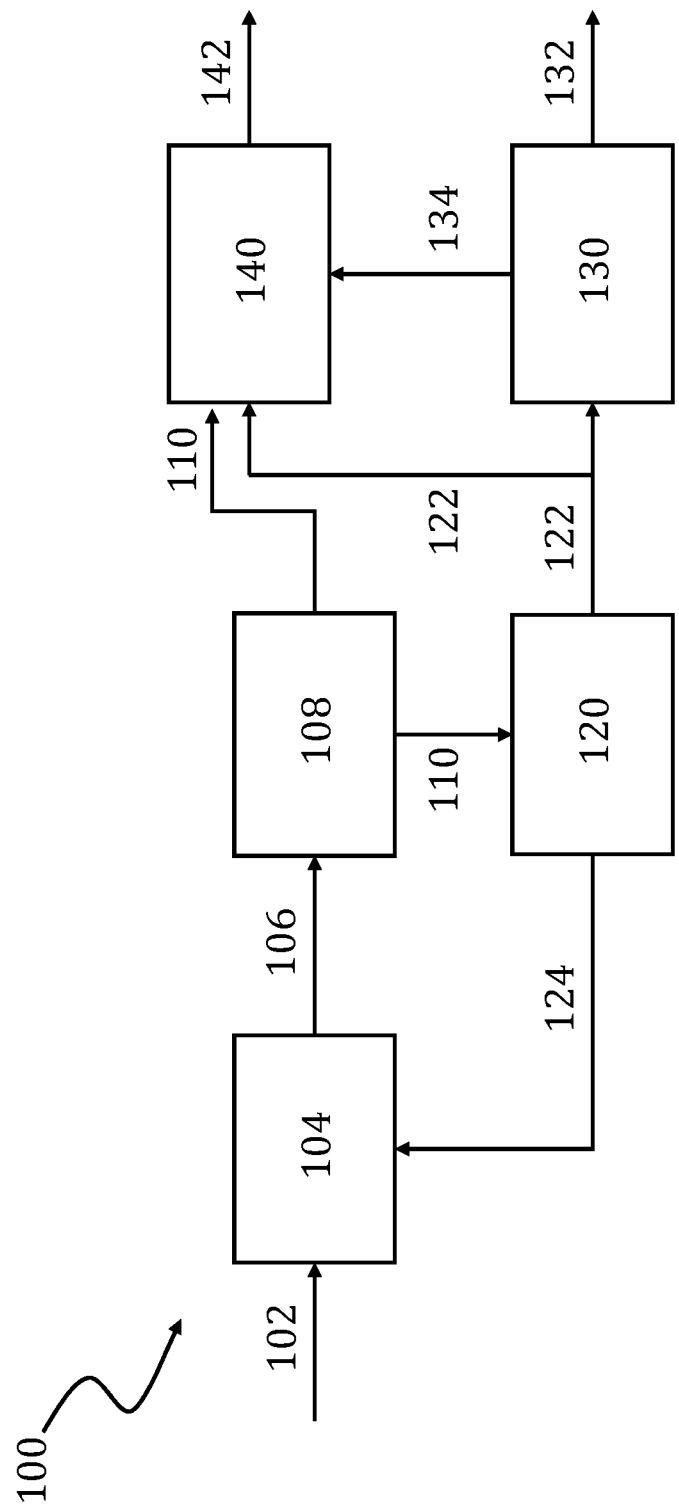
FIG. 1 depicts a system including coupled separation apparatuses and other components to produce a high-purity fructose fraction and mid-purity fructose fraction according to embodiments of the disclosure.

A high purity, fructose extract exhibiting a fructose purity in excess of about 95% by weight, such as exceeding a fructose purity of about 97% by weight, is disclosed. A method for maintaining overall fructose productivity using an SMB system including two or more SMB separators is also disclosed. The fructose is recovered from a feed stream. The method minimizes oligosaccharides in the feed stream that are directed to an isomerization chamber of the SMB system when recycling the SMB raffinate. The method minimizes the water utilized by the SMB system to lower the energy cost of evaporating the fructose extract. The SMB system maximizes production of about 97% by weight or higher purity fructose extract while allowing flexibility to adapt to shifting market demands of HFCS-97 relative to HFCS-55. The reduction in SMB water usage while maintaining the productivity of fructose-rich extract from the SMB system provides an economic advantage to the overall HFCS-55 production in the form of energy savings. The fructose extract may then be crystallized to produce anhydrous crystalline fructose or utilized as a raw material for downstream conversion to other products.

The system is used to produce fructose exhibiting a purity of greater than or equal to about 95% by weight utilizing two or more SMB separators coupled to one another in series. The first SMB separator processes a feedstock containing glucose, fructose, and one or more additional components that are inert to isomerization to produce an extract containing from at least about 80% by weight fructose to about 94% by weight fructose on a dry basis. The additional component(s) of the feedstock may be inert to isomerization to fructose. In other words, the additional component(s) may exhibit an inability to be isomerized into fructose. The feedstock may include from about 3% by weight to about 18% by weight of the components that are inert to isomerization to fructose. By way of example only, the feedstock may contain glucose, fructose, and higher polysaccharides (including, but not limited to, HFCS-42 or inverted sucrose syrups). A glucose-rich raffinate stream from the first SMB separator is introduced to an isomerization chamber. A second SMB separator processes a fraction of the fructose enriched extract from the first SMB separator to produce a high purity fructose extract of greater than or equal to about 95% by weight (and in some embodiments about 97% or greater purity by weight) and a raffinate including fructose from about 55% to about 90% fructose purity by weight. In some embodiments, the fructose raffinate may be combined (e.g., blended) with HFCS-42 to produce HFCS-55. In some embodiments, the first SMB separator is configured to allow about 20% of oligosaccharides (by weight) to exit the first SMB separator in the fructose extract, which decreases the oligosaccharides introduced to the isomerization chamber. The second SMB separator is configured to produce the high purity fructose extract including about 95% or greater fructose purity by weight of the total dissolved solids on a dry solids basis (and in some embodiments 97% or greater fructose purity) while minimizing water usage. The raffinate of the second SMB separator functions as a second outlet of oligosaccharides from the isomerization recycle loop and produces saleable HFCS-55 product.

Although the description describes high purity fructose production via corn starch hydrolysis, the disclosure is not limited to corn starch-based materials and may be applied to other feedstocks rich in fructose including inverted sucrose syrups.

Figure 2:
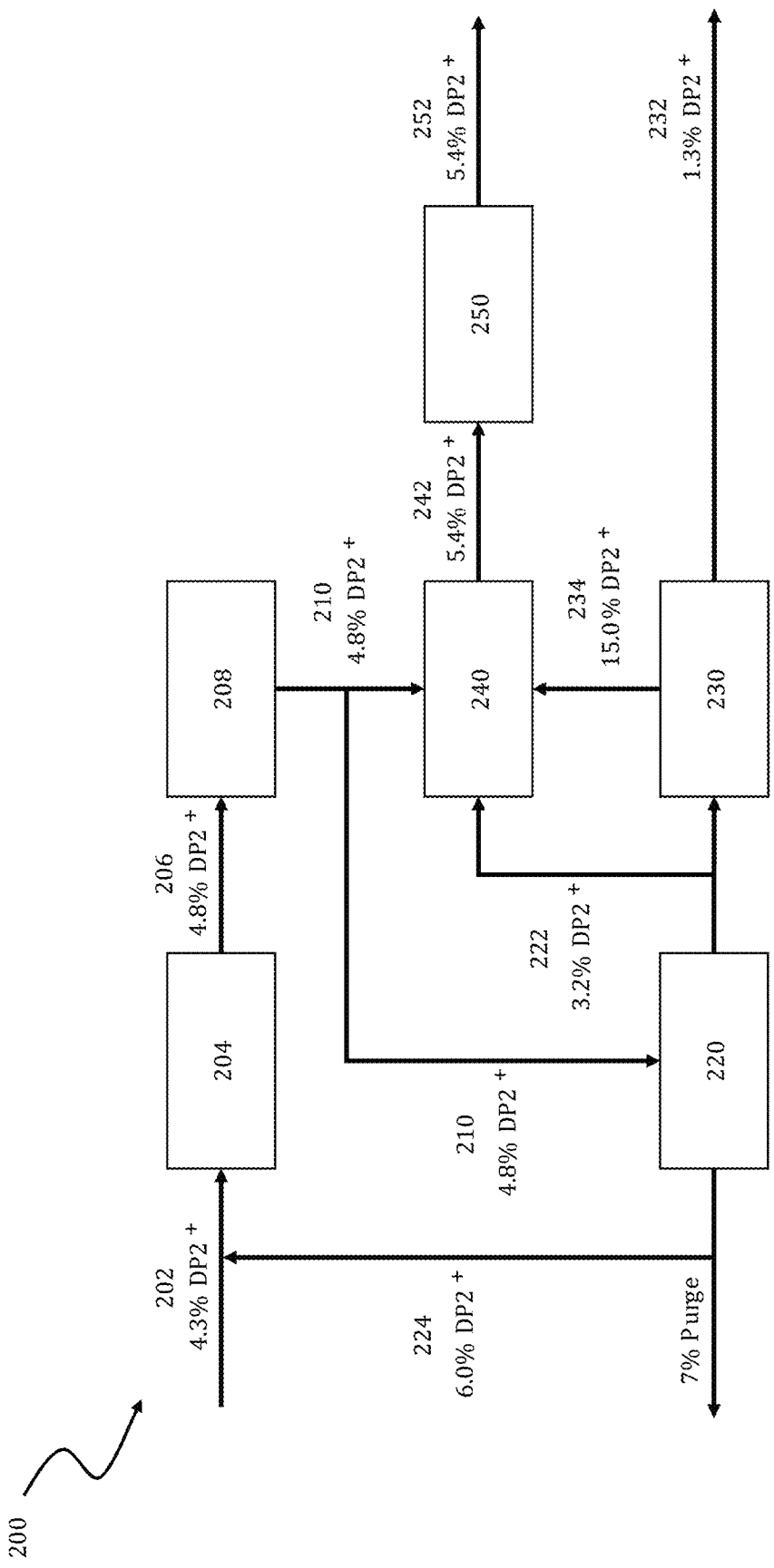
FIG. 2 depicts an SMB coupled-loop system to produce HFCS-95 (or greater purity) and HFCS-55 according to embodiments of the disclosure.
Figure 3:
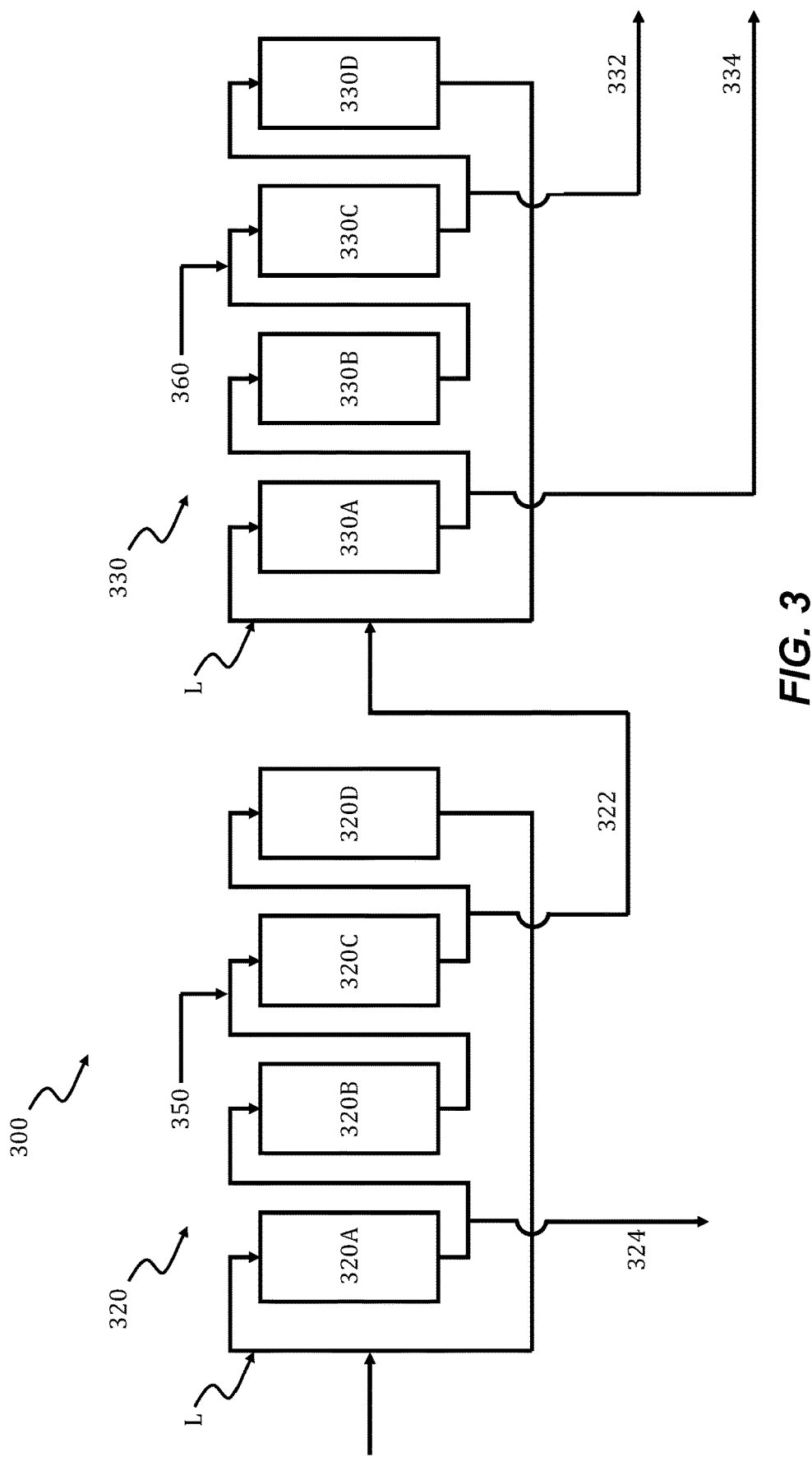
FIG. 3 depicts a coupled-loop system for producing both HFCS-55 and HFCS-95 with very low water usage according to embodiments of the disclosure.

Embodiments of the disclosure may be used to produce the high purity fructose extract using two or more coupled separators, such as SMB separators. In some embodiments, a process in which a 60% by weight dissolved solids solution of HFCS-42 is purified by the SMB system containing two SMB separators coupled in series is illustrated in FIG. 2. In FIGS. 2 and 3, the fructose purity of a high fructose corn syrup feedstock is designated by HFCS-X, where "X" denotes the percentage of fructose on a dry solids basis and the "+" denotes that the percentage may be greater than or equal to the indicated percentage. While two SMB separators are shown in FIG. 2, three or more SMB separators may be coupled in series. An SMB system of two SMB separators coupled in series is shown in FIG. 3.

As used herein, "about" or "approximately" in reference to a numerical value for a particular parameter is inclusive of the numerical value and a degree of variance from the numerical value that one of ordinary skill in the art would understand is within acceptable tolerances for the particular parameter. For example, "about" or "approximately" in reference to a numerical value may include additional numerical values within a range of from 90.0 percent to 110.0 percent of the numerical value, such as within a range of from 95.0 percent to 105.0 percent of the numerical value, within a range of from 97.5 percent to 102.5 percent of the numerical value, within a range of from 99.0 percent to 101.0 percent of the numerical value, within a range of from 99.5 percent to 100.5 percent of the numerical value, or within a range of from 99.9 percent to 100.1 percent of the numerical value.

As used herein, the term "high purity fructose" refers to the concentration of fructose in a fluid stream that includes at least about 95% by weight of the total dissolved solids on a dry solids basis.

As used herein, the term "mid-purity fructose" refers to the concentration of fructose in a fluid stream that includes from about 55% by weight to about 90% by weight of the total dissolved solids on a dry solids basis.

As shown in FIG. 1, a system 100 includes an isomerization chamber 104, an optional evaporator 108, a first separator 120, a second separator 130, and a mixer 140. The system 100 is configured to generate a high purity fructose product 132 and a mid-purity fructose product 142 from a feedstock (e.g., a precursor fluid stream to feed stream 102). The feedstock may undergo an initial treatment, where complex sugars in the feedstock are digested to give a feed stream 102. The feed stream 102 is introduced into and passes through the isomerization chamber 104, where glucose in the feed stream 102 is converted into fructose, forming isomerized product 106. After exiting the isomerization chamber 104, the isomerized product 106 passes into and through the first separator 120, which contains a chromatographic medium to separate the fructose from the glucose, to produce a fructose fraction 122 and a glucose-rich fraction 124. The glucose-rich fraction 124 is recycled back to the isomerization chamber 104 for further conversion to fructose. The system 100 also includes inlets, outlets, pipes, valves, etc. to transport the fluid streams through the system 100. While not illustrated or described in detail, the system 100 includes additional components (e.g., pipelines, line filters, valves, temperature detectors, flow detectors, pressure detectors, and the like).

Feedstocks containing complex polysaccharides, such as starch extracts from barley or corn syrup, may be used as the feedstock (e.g., a source) for glucose and fructose. The feedstock may, for example, be initially treated with α-amylase and/or β-glucanase to break down the complex saccharides into smaller soluble sugar components, producing the feed stream 102. Glucoamylase may be used to further digest the smaller soluble sugar components into individual sugar monomers, such as glucose or fructose in the feed stream 102. Afterwards, the feed stream 102 containing the small, soluble sugar components may be introduced (e.g., fed) into the isomerization chamber 104.

The feed stream 102 passes through the isomerization chamber 104, where glucose is converted to fructose either by acid hydrolysis or enzymatic catalysis. The isomerization reaction may be catalyzed by glucose isomerase (D-glucose-6-phosphate isomerase). The glucose-containing feed stream 102 is mixed with the glucose isomerase (GI) to produce a reaction solution, so that a portion of the glucose undergoes conversion to fructose to generate the isomerized product 106. Glucose isomerase may be immobilized on a resin, which is contained in the isomerization chamber 104 in, for example, a chromatographic column. The glucose isomerase may be any commercially available version as is known in the art, such as OPTISWEET® 22 (adsorbed glucose isomerase on $SiO_2$ and crosslinked to glutaraldehyde; from Miles Kali-Chemie, GmbH & Co.), SPEZYME® (crystallized crosslinked glucose isomerase adsorbed to granular diethyl-aminoethyl(DEAE)-cellulose resin; from Genencor, Inc./DuPont et Nemours, Inc.), GENSWEET® SGI (glucose isomerase adsorbed onto DEAE-cellulose resin; Genencor, Inc./Dupont et Nemours, Inc.), or GENSWEET® IGI (polyethyleneimine and glutaraldehyde crosslinked cells expressing glucose isomerase mixed with bentonite clay and diatomaceous earth; from Genencor, Inc./Dupont et Nemours, Inc.). The temperature within the isomerization chamber may range from about 40° C. to about 90° C., such as from about 65° C. to about 70° C. The pH of the reaction solution in the reaction chamber may range from 8.0-8.5.

The isomerized product 106 may, optionally, be further processed by passing the isomerized product 106 through a gel filtration medium or a size exclusion chromatographic medium to remove larger undigested sugars. The size exclusion chromatographic medium may be a commercially available product including, but not limited to, SEPHACRYL® resin (Millipore Sigma) and SEPHADEX® resins (Millipore Sigma).

The isomerized product 106 may, optionally, be passed through the evaporator 108 before proceeding to the first separator 120 or may be introduced directly to the first separator 120. In the evaporator 108, the isomerized product 106 may be heated to a temperature of from about 80° C. to 120° C., such as from about 90° C. to about 110° C. The evaporator 108 concentrates the isomerized product 106 by removing water to generate a concentrated product 110, which exits the evaporator 108. When the concentrated product 110 in the evaporator 108 achieves from about 40% to about 80% fructose by weight on a dry solids basis, a portion of the concentrated product 110 may be transferred to the first separator 120, while another portion may be transferred to the mixer 140. The portion of the concentrated product 110 that is transferred to the mixer 140 is combined with other higher-purity fructose components to generate a commercially viable mid-purity fructose product 142. The other portion of the concentrated product 110 is transferred to the first separator 120.

The first separator 120 include a chromatographic medium that is formulated to separate the fructose from the glucose. Chromatographic media suitable for use include, but are not limited to, cation exchange resins such as DIAION™ UBK535 (Ca) (Mitsubishi Chemicals), DIAION™ UBK530 (Na) (Mitsubishi Chemicals), Rohm and Haas AMBERLITE™ resins, PUROLITE® PCR resins, and DOWEX® MONOSPHERE® chromatographic resins. The concentrated product 110 passes through the chromatographic medium in the first separator 120 to generate a fructose fraction 122 and a glucose fraction 124, the latter of which is passed back through the isomerization chamber 104 to further increase the fructose content by converting additional glucose in the glucose fraction 124 to fructose. The first separator 120 may be operated at a temperature of from about 50° C. to about 75° C., such as from about 60° C. and about 70° C.

A portion of the fructose fraction 122 is transferred to the mixer 140. After exiting the first separator 120, the fructose fraction 122 may be introduced to a second separator 130, which contains a chromatographic medium formulated to separate the fructose from the fructose fraction 122 to yield the high purity fructose product 132. The chromatographic medium of the second separator 130 may be the same as or different from the chromatographic medium used in the first separator 120. The first separator 120 may include inlets that enable eluents, such as deionized water or buffer, to enter the first separator 120 and control the composition of the eluted fractions 124 and 122.

The second separator 130 also generates a less pure fructose fraction 134 that exhibits a lower purity of fructose and other components, such as oligosaccharides. The less pure fructose fraction 134 may be combined with the portion of the fructose fraction 122 from the first separator 120 in the mixer 140 to generate a commercially useful mid-purity fructose product 142. The mid-purity fructose product 142 has a lower fructose purity than the high purity fructose product 132 collected from the second separator 130. The fructose content of the high purity fructose product 132 may be at least about 90% fructose by weight on a dry goods basis, such as at least about 95% fructose by weight on a dry goods basis or at least about 97% or more fructose by weight on a dry goods basis. The fructose content of the mid-purity fructose product 142 may be at least about 45% fructose by weight on a dry goods basis, such as about 50% or more fructose by weight on a dry goods basis or about 75% or more fructose by weight on a dry goods basis. The second separator 130 may be operated at a temperature of from about 50° C. to about 75° C., preferably between about 60° C. and about 70° C.

The second separator 130 may have inlets that allow eluents, such as deionized water or buffer, to enter the second separator 130 and control the composition of the eluted fractions, the high purity fructose product 132 and less pure fructose fraction 134, as described above for the first separator 120.

The less pure fructose fraction 134 is transferred to the mixer 140, where the less pure fructose fraction 134 may be mixed with the fructose fraction 122 from the first separator 120 and the concentrated product 110 from the evaporator 108. The relative amounts of these three inputs may be adjusted to obtain a mid-purity fructose product 142, having a predetermined fructose content by weight, such as from about 55% to about 90% by weight. Thus, the system 100 produces two products—the high purity fructose product 132 and the mid-purity fructose product 142—from one feed stream 102 by passing the feed stream 102 through a closed system including the coupled separators 120 and 130. In some embodiments, the high purity fructose product 132 is HFCS-95$^+$ and the mid-purity fructose product 142 is HFCS-55$^+$.

In some embodiments, as shown in FIG. 2, the SMB system 200 passes a glucose-containing feed stream 202, such as corn syrup, through an isomerization chamber 204, a first evaporator 208, a first SMB separator 220, a second SMB separator 230, a mixer 240, and a second evaporator 250 to yield a high purity fructose extract 232, such as HFCS-95$^+$, and a mid-purity fructose product 252, such as HFCS-55$^+$.

The glucose-containing feed stream 202 is transported to the isomerization chamber 204, where the glucose is converted to fructose either by acid hydrolysis or enzymatic catalysis as described above for FIG. 1. The feed stream 202 may also include a portion of higher oligosaccharides (e.g., DP2$^+$), such as about 4.3% by weight oligosaccharides of the total feed stream 202 composition. The glucose-containing feed stream 202 is mixed with glucose isomerase (GI) in the isomerization chamber 204, so that a portion of the glucose undergoes conversion to fructose to yield an isomerized product 206. The isomerized product 206 may also include an oligosaccharide (e.g., DP2$^+$) content, such as about 4.8% by weight. The temperature and pH of the isomerization chamber 204 are as described above.

The isomerized product 206 is transported from the isomerization chamber 204 and to the evaporator 208. In the evaporator 208, heat is applied to the isomerized product 206 to remove a portion of the eluent to give a concentrated product 210 having dry solids and an oligosaccharide (e.g., DP2$^+$) content of about 4.8% by weight, for example. The evaporator 208 may heat the isomerized product 206 to a temperature of from about 90° C. to 150° C., preferably 95° C. to 120° C. to remove water. When the dry solids concentration reaches about 40% to about 80% by weight, such as about 70% to about 75% by weight (on a dry solids basis), the concentrated product 210 is generated. A portion of the concentrated product 210 is transferred to the first SMB separator 220, and another portion of the concentrated product 210 is transferred separately to the mixer 240.

The first SMB separator 220 is configured to produce a high quality, e.g., high purity, glucose-rich raffinate 224 feed stream for recycling to the isomerization chamber 204 of the SMB system 200 to remove additional glucose. The glucose-rich raffinate 224 feed stream may have an oligosaccharide (e.g., DP2$^+$) content of about 6.0% by weight, for example. This is achieved by maximizing the percentage of oligosaccharides that elute in the fructose extract 222, while maintaining an extract fructose purity ranging from about 80% to about 94% by weight. The first SMB separator 220 also produces a fructose extract 222 that may be fed into the mixer 240 and the second SMB separator 230. The fructose extract 222 may exhibit an oligosaccharide (e.g., DP2$^+$) of 3.2% by weight. In the second SMB separator 230, the fructose extract 222 undergoes further separation and purification to form a high purity fructose product 232 and a fructose raffinate 234. A portion of the fructose extract 222 is fed into the mixer 240, where it is mixed with other components, such as a low-purity fructose component, such as HFCS-42. A portion of the glucose-rich raffinate 224, such as 7% by weight, is purged or removed to minimize the amount of oligosaccharides present.

When producing high purity fructose by conventional techniques, one of ordinary skill in the art would need to use an excess of eluent to prevent the contamination of the fructose-rich extract by oligosaccharides. However, this would cause unacceptable levels of oligosaccharides to accumulate in the recycled glucose-rich raffinate, which would preclude the isomerization chamber from effectively producing HFCS-42 to subsequently be used as feed into the SMB separator. However, in embodiments according to the disclosure, a minimal amount of eluent, such as water, is used to ensure sufficient fructose extract purity is introduced into the SMB system. Minimizing the amount of water used in the separation process enables a larger percentage of oligosaccharides to accumulate within the fructose extract 222, which lowers the quantity of oligosaccharides recycled in the raffinate to the isomerization chamber 204. This ensures that the glucose-rich raffinate 224 introduced to the isomerization chamber 204 is an acceptable purity such that the isomerization reaction is able to achieve a 42% fructose purity (by weight of the total dissolved solids on a dry solids basis) and to produce HFCS-42 with a sufficiently short residence time within the isomerization chamber 204 so as to not limit the fructose productivity of the overall process.

A portion of the fructose extract 222 produced by the first SMB separator 220 is introduced to the second SMB separator 230 in order to produce the high purity fructose extract 232, which contains greater than or equal to about 95% fructose purity, such as greater than or equal to about 97% fructose purity or greater than or equal to about 98% fructose purity, by weight on a dry basis. The high purity fructose product 232 may have an oligosaccharide (e.g., $DP2^+$) content of about 0.1% to about 10% by weight on a dry solids basis, such as 1.3% by weight oligosaccharides. The high purity fructose extract 232 may be a HFCS-95$^+$ extract. In addition to the high purity fructose extract 232, the second SMB separator 230 may produce a second oligosaccharide bleed stream in the form of a valuable fructose raffinate 234. In this embodiment, minimal eluent is supplied to the second SMB separator 230 to enable a concentration of fructose in the fructose raffinate 234 to be adjusted in a controllable manner, which may increase the fructose purity of the fructose raffinate 234 to between about 70% and about 90% by weight. The oligosaccharide (e.g., $DP2^+$) content of the fructose raffinate 234 may be about 5% to about 30% by weight on a dry solids basis. The elevated fructose purity ensures that the fructose raffinate 234 from the second SMB separator 230 is of sufficiently high quality for downstream blending operations to produce other valuable fructose-based products, such as HFCS-55. Being able to vary the purity of the fructose raffinate 234 from the second SMB separator 230 also imparts flexibility to respond to varying market demands for HFCS-95$^+$/HFCS-97$^+$ and HFCS-55. While FIG. 2 describes producing HFCS-95$^+$ and HFCS-55, the high purity fructose extract 232 from the second SMB separator 230 may exhibit a higher purity (greater than or equal to about 97% fructose purity by weight of the total dissolved solids on a dry solids basis or greater than or equal to about 98% fructose purity), and the raffinate stream 234 from the second SMB separator 230 may exhibit a higher fructose purity (between about 70% and about 90% by weight of the total dissolved solids on a dry solids basis). The raffinate stream 234 from the second SMB separator 230 may be combined, for example, with the fructose extract 222, such as HFCS-42, to produce the mixed product 242, such as HFCS-55. By adjusting the purity of the fructose raffinate stream 234 exiting the second SMB separator 230 and combining the fructose raffinate stream 234 from the second SMB separator 230 with the fructose extract 222 of a different fructose purity, the fructose raffinate stream 234 from the second SMB separator 230 may be used to form fructose-based products comprising different fructose purities.

The chromatographic media in the two SMB separators 220 and 230 are as described for the first separator 120 and second separator 130 above.

The other portion of the concentrated product 210 is transported from the evaporator 208 to the mixer 240, where the concentrated product 210 is combined with the fructose extract 222 from the first SMB separator 220 and the fructose raffinate 234 from the second SMB separator 230. The relative amounts of the concentrated product 210, fructose extract 222, and fructose raffinate 234 may be selected to achieve a particular composition of fructose in the mixed product 242, which is a precursor to the mid-purity fructose product 252 having a fructose content ranging from 55% to 90% by weight on a dry goods basis. The mixed product 242 has a lower fructose content on a dry goods basis than the high purity fructose extract 232 obtained from the second SMB separator 230. The mixed product 242 passes through a second evaporator 250 to concentrate the mixed product 242 to yield the mid-purity fructose product 252. The second evaporator 250 heats the mixed product 242 to a temperature of from about 90° C. to 150° C., such as from about 95° C. to about 120° C. When the dry solids concentration reaches between about 40% and about 80% by weight, such as between about 70% and about 75% by weight (on a dry solids basis), the mid-purity fructose product 252 is generated. In some embodiments, the mixed product 242 is sufficient for use, circumventing the need for the second evaporator 250.

FIG. 3 illustrates other embodiments for the production of a high purity fructose extract 332, e.g., HFCS-95$^+$, and a mid-purity fructose product, e.g., HFCS-70$^+$, in SMB system 300 after introducing a relatively low purity fructose feed HFCS-42 into the SMB system 300, which includes a first SMB sub-system 320 and second SMB sub-system 330 that are coupled via a closed loop. The first SMB sub-system 320 may be similar to the first SMB separator 220 as in the system 200. The second SMB sub-system 330 may be similar to the second SMB separator 230 as in the system 200. Each of the SMB sub-systems 320 and 330 may include multiple (e.g., four or more) chromatographic columns, 320A-320D and 330A-330D, containing chromatographic media, as described above for the SMB separators 220 and 230. For example, the concentrated product 210 of system 200 may be introduced into the first SMB sub-system 320 of system 300. The first SMB sub-system 320 may be configured to receive the isomerized product 206. In the first SMB sub-system 320, the HFCS-42 product 210 passes via a closed loop L into a first chromatographic column 320A to separate fructose from glucose, where a glucose-rich raffinate is collected and fed into an isomerization chamber to increase the amount of fructose in the raffinate. The remaining fructose-rich fraction is passed through a second column 320B for further separation. Similar separations may be conducted through third and fourth columns 320C, 320D. Prior to passing through the third column 320C of the first SMB sub-system 320, a minimal amount of eluent 350 (e.g., deionized water) may be introduced to elute the fructose extract 322. As the fructose solution becomes more concentrated, the viscosity of the solution increases, which can negatively impact separation. For example, passing viscous samples through the column can lead to pressure build up and column breakage. The remaining components pass through the fourth column 320D before mixing with another portion of the HFCS-42 feed stream.

As illustrated in FIG. 3, the closed loop L connects the first chromatographic column 320A, second column 320B, third column 320C, and fourth column 320D and recirculates the mobile phase (e.g., deionized water or buffer) through the first SMB sub-system 320.

The fructose extract 322, such as HFCS-90+, undergoes further separation in the second SMB sub-system 330. After eluting from the first SMB sub-system 320, the fructose extract 322 is transferred to the first column 330A of the second SMB sub-system 330. The fructose raffinate 334 is collected after it elutes from the first column 330A transferred to a mixer, where the fructose raffinate 334 has 70% to 90% fructose on a dry weight basis. The remaining fructose-rich fraction passes through a second column 330B to further separate fructose from the other components, such as glucose or oligosaccharides, in solution. Between the second and third columns 330B, 330C, a predetermined amount of eluent 360, such as deionized water, is added to the feed stream, such that some of the high-purity fructose extract 332 bleeds into the oligosaccharide and glucose-containing fractions, which enables control over the fructose content of the other fractions for downstream use. The high purity fructose extract 332 is eluted and collected.

The method utilizing the SMB system is used to enrich (e.g., purify) material containing both glucose, fructose, and higher molecular weight saccharides using SMB chromatography to produce the high purity, fructose extract. The method comprises purifying high fructose corn syrup from a 42% purity by weight fructose into three product streams.

The first product stream (e.g., the glucose-rich fraction 124, the glucose-rich raffinate 224, and the glucose-rich raffinate 324) is rich in glucose and may be recycled to the isomerization chamber to produce additional fructose from glucose. The second product stream (e.g., the high purity fructose product 132, the high purity fructose extract 232, and the high purity fructose extract 332) is the fructose extract exceeding a purity of about 95% by weight, such as exceeding a purity of about 97% by weight or exceeding a purity of about 98% by weight. The third product stream (e.g., the fructose fraction 122, the fructose extract 222, and the fructose extract 322) may range from about 55% to about 90% fructose purity by weight on a dry solids basis and may be blended with 42% fructose syrup to produce saleable high fructose corn syrup of 55% fructose purity by weight on a dry solids basis. The systems and methods according to embodiments of the disclosure reduces water usage, improves resin productivity, maximizes overall glucose conversion to saleable fructose, and minimizes energy cost by lowering the evaporation requirements to produce syrups with a high dissolved solids content, increasing the productivity and profitability achieved by the SMB system. In addition, the fructose extract may be produced in a liquid form and at a high purity without conducting a crystallization act.

The flow rates of the feedstock and streams passing through the individual compartments of the system may vary based on the desired fructose composition of the high purity fructose extract and the mid-purity fructose product. Generally, the SMB operates under flow rates of about 0.8-2.0 bed volume per hour (0.0022-0.0056 bed volume per second), where the flow rate for each individual SMB component (e.g., column or zone) may be the same or different. In some embodiments, the flow rates applied range from about 25 mL/min (about 0.45 mL/s) to about 100 mL/min (about 1.67 mL/s).

The following examples serve to explain embodiments of the disclosure in more detail. These examples are not to be construed as being exhaustive or exclusive as to the scope of this disclosure.

Example 1

As Applied to HFCS-42 Purification

A 60% dissolved solids solution of HFCS-42 produced from isomerization of a glucose-rich feedstock was treated by embodiments of the method according to the disclosure. In other embodiments, the fructose-rich feed may originate from other sources including, but not limited to, invert syrup from sucrose solutions or mother liquor from fructose crystallization. An extract fraction including fructose at greater than or equal to about 97% purity on a dry solids basis was obtained. A pilot scale simulated moving bed system was used for the separation and was configured as illustrated in FIG. 2. In the context of operating an SMB unit, "step" is herein defined as the subset of operation wherein the feedstock is introduced (e.g., injected) into a single column upon which at the end of the "step" the configuration of valves advances such that material is introduced into the next downstream column within the recirculation loop. The SMB separation of the SMB system was operated such that each step was divided into two sub-periods as described in U.S. Pat. No. 5,102,553, the disclosure of which is incorporated by reference herein. The first sub-period encompassed a span of time where the feedstock and eluent were injected into distinct columns within the recirculation loop. Concurrently, extract and raffinate fractions were also withdrawn from the SMB separator at defined points. During the second sub-period, the internal solids profile within the SMB separator recirculated through the SMB system without any additional material added or removed from the SMB separator. Both SMB separators were filled with Mitsubishi UBK-535 resin in the calcium form. The first SMB separator was loaded at approximately 125 lbs dissolved solids per cubic foot resin per day (approximately $2.3 \times 10^{-5}$ grams dissolved solids per cubic centimeter per second) while the second SMB separator was loaded at approximately 200 lbs dissolved solids per cubic foot resin per day (approximately $2.7 \times 10^{-5}$ grams per cubic centimeter per second). The total resin volume for this experiment was 2.30 cubic feet ($3.0 \times 10^4$ cubic centimeters) per separator distributed amongst 8 columns. The additional operating parameters of the system containing the first and second SMB separators are listed in Table 1.

TABLE 1

| SMB 1 Operating Parameters | | |
|---|---|---|
| Resin Solids Loading | (lb DS/ft³ resin/day) | 123.33 |
|  | (g DS/cm³ resin/s) | $2.3 \times 10^{-5}$ |
| Water-to-Feed Ratio | (volume ratio) | 0.92 |
| Extract-to-Raffinate Ratio | (volume ratio) | 0.51 |
| SMB 2 Operating Parameters | | |
| Resin Solids Loading | (lb DS/ft³ resin/day) | 50.85 |
|  | (g DS/cm³ resin/s) | $9.4 \times 10^{-6}$ |
| Water-to-Feed Ratio | (volume ratio) | 0.62 |
| Extract-to-Raffinate Ratio | (volume ratio) | 0.83 |

TABLE 2

| Stream | Dissolved Solids (%) | Fructose Purity (g/100 g DS) | Glucose Purity (g/100 g DS) | DP2 + Content (g/100 g DS) | Fructose Recovery (%) | Glucose Recovery (%) | DP2 + Elimination (%) |
|---|---|---|---|---|---|---|---|
| SMB 1 Performance | | | | | | | |
| Feed | 60.40 | 42.76 | 51.50 | 5.74 | 95.70 | 96.46 | 83.02 |
| Extract | 44.25 | 93.72 | 4.19 | 2.09 | | | |
| Raffinate | 30.83 | 3.27 | 88.79 | 7.94 | | | |
| SMB 2 Performance | | | | | | | |
| Feed | 42.32 | 93.10 | 3.71 | 3.19 | 75.25 | 86.23 | 55.34 |
| Extract | 41.73 | 97.22 | 0.68 | 2.10 | | | |
| Raffinate | 15.09 | 82.33 | 10.97 | 6.70 | | | |

The SMB system including the first and second SMB separators was operated until chemical equilibrium and steady-state operation were attained. The two SMB separators were used to produce the fructose extract having a greater than about 97% purity. The results are reported in Table 2.

The recovery values of glucose and fructose in Table 2 only detail the recoveries of glucose and fructose into the respective SMB streams and not to the overall process. For this example, the overall fructose recovery into usable product was about 99.9%. The fructose extract stream produced by the second SMB separator contained about 98% purity fructose which exceeded the goal of greater than about 97% fructose purity. This high-quality fructose extract is suitable for downstream processing, such as crystallization or chemical conversion into other high-value products. The glucose-rich raffinate from the first SMB separator was suitable for recycling to the isomerization columns (in this case 93% of the raffinate was assumed to be recycled and 7% was purged from the recycle loop) and the fructose-rich raffinate from the second SMB separator was acceptable for blending with HFCS-42 to produce saleable HFCS-55. While FIG. 2 describes producing HFCS-95 and HFCS-55, the high purity fructose extract 232 from the second SMB separator may exhibit a higher purity (greater than or equal to about 97% fructose purity or greater than or equal to about 98% fructose purity) and the raffinate stream 234 from the second SMB separator may exhibit a higher fructose purity (between about 70% and about 90%).

Example 2

Comparison to One SMB Separator with Raffinate Recycle

The embodiment of the disclosure described in Example 1 was compared to a conventional process to produce a fructose extract using a single SMB separator with 93% of the glucose-rich raffinate recycled to the isomerization columns and the remainder purged. In order to study only the effects of recycling the glucose-rich raffinate back to the isomerization columns, it was assumed that the isomerization columns were able to produce HFCS-42 regardless of the oligosaccharide content of the dextrose feed. Experimentally, the oligosaccharide content of the HFCS-42 processed by the single SMB separator was artificially elevated using corn syrup solids which contained, on a dry solids basis, 8% glucose, 56% maltose, 16% maltotriose, and 20% higher saccharides. The conventional SMB separator was operated at a lower loading of about 75 lbs dissolved solids per cubic foot of resin per day (about $1.4 \times 10^{-5}$ grams dissolved solids per cubic centimeter per second) in order to improve the fructose extract purity and recovery. The operating parameters for the conventional SMB separator are listed in Table 3.

Based on the calculated oligosaccharide elimination from the high purity extract stream and a material balance of the overall process, the steady-state oligosaccharide dry solids content of the HFCS-42 processed by the conventional SMB separator was determined to be 17.5%. The performance of the conventional SMB separator is reported in Table 4.

TABLE 3

| SMB Operating Parameters | | |
|---|---|---|
| Resin Solids Loading | (lb DS/ft³ resin/day) | 73.86 |
| | (g DS/cm³ resin/s) | $1.4 \times 10^{-5}$ |
| Water-to-Feed Ratio | (mass ratio) | 2.23 |
| Extract-to-Raffinate Ratio | (mass ratio) | 0.50 |

TABLE 4

SMB Performance

| Stream | Dissolved Solids (%) | Fructose Purity (g/100 g DS) | Glucose Purity (g/100 g DS) | DP2 + Content (g/100 g DS) | Fructose Recovery (%) | Glucose Recovery (%) |
|---|---|---|---|---|---|---|
| Feed | 60.10 | 42.00 | 40.55 | 17.46 | 99.10 | 99.76 |
| Extract | 27.90 | 97.73 | 0.24 | 2.04 | | |
| Raffinate | 19.30 | 0.66 | 69.34 | 30.00 | | |

To prevent the oligosaccharides from contaminating the high purity fructose extract, high volumes of water were consumed by the conventional SMB separator compared to the system according to the embodiment of Example 1. For the process described in Example 1, 5.23 pounds of water (2.37 kg) were used to produce one pound (453.6 g) of dry basis HFCS-97 while the conventional process used 6.77 pounds of water (3.07 kg) per pound of dry basis HFCS-97 produced. The system according to the embodiment of Example 1 thus used 23% less water to produce the high purity fructose extract compared to the conventional process. Furthermore, the second SMB separator of Example 1 was able to accommodate a relatively high loading of 200 lbs dissolved solids per cubic foot of resin ($3.7 \times 10^{-5}$ grams dissolved solids per cubic centimeter) per day which allows the process to use 57 cubic feet of resin ($7.5 \times 10^4$ cubic centimeters) per short ton of dry basis HFCS-97 produced compared to 63 cubic feet of resin ($8.3 \times 10^4$ cubic centimeters) per short ton of dry basis HFCS-97 for the conventional single loop process. Thus, the embodiment of the disclosure used 10% less resin to produce an equivalent amount of HFCS-97 compared to using the conventional SMB separator.

As noted above, due to the high oligosaccharide elimination in Example 2, the isomerization columns would be unable to produce HFCS-42 since the incoming dextrose feed would possess very high levels of oligosaccharides. Taking this into account, a single SMB separator producing high purity fructose would actually be required to purge 30% (rather than the 7% value used in Example 2) of the glucose-rich raffinate to ensure successful production of HFCS-42 from the isomerization columns. This would decrease the overall yield of fructose for the process to 73% compared to the 95% fructose yield obtained in Example 1. Therefore, the embodiment of Example 1 also maximizes the conversion of glucose into valuable high purity fructose.

The applicability of this disclosure is not limited by the examples described above. The disclosure may be useful for all applications involving the production of high purity fructose extract in which glucose-rich raffinate is to be re-isomerized.

While the disclosure is susceptible to various modifications and alternative forms, specific embodiments have been shown by way of example in the drawings and have been described in detail herein. However, the invention is not intended to be limited to the particular forms disclosed. Rather, the invention is to cover all modifications, equivalents, and alternatives falling within the scope of the invention as defined by the following appended claims and their legal equivalents.

What is claimed is:

1. A method for producing a first fructose product and a second fructose product, the method comprising:
   a) introducing a feed stream comprising glucose and fructose to an isomerization chamber to produce an isomerized product;
   b) introducing the isomerized product to a first simulated moving bed (SMB) separator to produce a first fructose fraction and a glucose fraction, the first fructose fraction exhibiting a fructose purity of from at least about 80% by weight to about 94% by weight;
   c) introducing the glucose fraction to the isomerization chamber to produce additional isomerized product;
   d) introducing the first fructose fraction to a second SMB separator to produce a first fructose product exhibiting a fructose purity of greater than or equal to about 95% by weight and to produce a second fructose fraction, the second fructose fraction having a fructose purity less than the first fructose product;
   e) producing a second fructose product by mixing the second fructose fraction from the second SMB separator and a portion of the isomerized product; and
   f) recovering the first fructose product.

2. The method of claim 1, wherein the second fructose fraction exhibits a fructose purity from about 70% by weight to about 90% by weight.

3. The method of claim 2, wherein the producing the second fructose product comprises mixing the second fructose fraction, the isomerized product, and a portion of the first fructose fraction.

4. The method of claim 2, wherein the second fructose product exhibits a fructose purity of from about 55% by weight to about 90% by weight.

5. The method of claim 1, wherein introducing the isomerized product to the first SMB separator comprises, before introducing the isomerized product to the first SMB separator, flowing the isomerized product through an evaporator to generate a concentrated isomerized product.

6. The method of claim 1, wherein introducing the first fructose fraction to the second SMB separator further comprises introducing an eluent to the second SMB separator to increase the fructose purity of the second fructose fraction.

7. A method of producing a fructose extract, the method comprising:
   a) introducing a feedstock comprising glucose, fructose, and one or more components inert to isomerization to fructose to a first simulated moving bed (SMB) separator of an SMB system to produce a first fructose extract and a glucose-rich raffinate;
   b) introducing the glucose-rich raffinate to an isomerization chamber to produce additional fructose;
   c) introducing the first fructose extract to a second SMB separator to produce a second fructose extract exhibiting a purity of greater than or equal to about 95% by weight and a fructose raffinate; and
   d) recovering the second fructose extract.

8. The method of claim 7, wherein introducing the first fructose extract to the second SMB separator comprises producing the fructose raffinate exhibiting a fructose purity of from about 55% by weight to about 90% by weight.

9. The method of claim 7, further comprising producing a fructose product using the fructose raffinate from the second SMB separator.

10. The method of claim 9, wherein producing the fructose product comprises combining the fructose raffinate from the second SMB separator and the first fructose extract from the first SMB separator to produce the fructose product exhibiting a fructose purity of from about 55% to about 90% by weight.

11. The method of claim 7, wherein introducing the first fructose extract to the second SMB separator to produce the second fructose extract comprises producing the second fructose extract exhibiting a purity of greater than or equal to about 97% by weight.

12. The method of claim 7, wherein introducing the first fructose extract to the second SMB separator to produce the second fructose extract comprises producing the second fructose extract exhibiting a purity of greater than or equal to about 98% by weight.

13. The method of claim 7, wherein introducing the glucose-rich raffinate to the isomerization chamber comprises using glucose isomerase to convert glucose in the glucose-rich raffinate to fructose, a fructose purity of the glucose-rich raffinate greater than or equal to about 42% by weight.

* * * * *